(12) United States Patent
Piers et al.

(10) Patent No.: US 7,137,702 B2
(45) Date of Patent: Nov. 21, 2006

(54) METHODS OF OBTAINING OPHTHALMIC LENSES PROVIDING THE EYE WITH REDUCED ABERRATIONS

(75) Inventors: Patricia Ann Piers, Groningen (NL); Sverker Norrby, Leek (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 10/768,755

(22) Filed: Jan. 30, 2004

(65) Prior Publication Data

US 2004/0183996 A1    Sep. 23, 2004

Related U.S. Application Data

(62) Division of application No. 10/027,703, filed on Dec. 21, 2001, now Pat. No. 6,705,729.

(60) Provisional application No. 60/259,981, filed on Jan. 5, 2001.

(30) Foreign Application Priority Data

Dec. 22, 2000  (SE)  .................................. 0004829

(51) Int. Cl.
  *G02C 7/02*  (2006.01)
(52) U.S. Cl. ..................... 351/177; 623/6.11; 623/6.23
(58) Field of Classification Search ............... 351/159, 351/168, 176–7, 177; 623/6.11, 6.13, 6.23, 623/6.24, 6.27; 606/4, 5

See application file for complete search history.

(56) References Cited

U.S. PATENT DOCUMENTS

| | | | | |
|---|---|---|---|---|
| 5,019,098 | A | 5/1991 | Mercier | 623/6.24 |
| 5,173,723 | A * | 12/1992 | Volk | 351/161 |
| 5,282,852 | A | 2/1994 | Capetan et al. | 623/6.11 |
| 5,777,719 | A | 7/1998 | Williams et al. | 351/212 |
| 5,891,131 | A | 4/1999 | Rajan et al. | 605/5 |
| 5,968,095 | A | 10/1999 | Norrby | 128/898 |
| 6,183,084 | B1 * | 2/2001 | Chipman et al. | 351/176 |
| 6,224,628 | B1 * | 5/2001 | Callahan et al. | 623/6.4 |
| 6,413,276 | B1 | 7/2002 | Werblin | 623/6.23 |
| 6,554,425 | B1 * | 4/2003 | Roffman et al. | 351/177 |
| 6,609,793 | B1 | 8/2003 | Norrby et al. | 351/212 |

FOREIGN PATENT DOCUMENTS

| | | |
|---|---|---|
| WO | WO9635396 | 11/1996 |
| WO | WO9831299 | 7/1998 |
| WO | WO0189424 | 11/2001 |

OTHER PUBLICATIONS

Rowsey et al, Dutton et al, editors, *Survey of Ophthalmology*, 43(2):147-156 (1998).
Atchison. Optical design of intraocular lenses. I. On-axis performance. *Optometry & Vision Science*. vol. 66, No. 8, pp. 492-506.
Atchison. Optical design of intraocular lenses. II. On-axis performance. *Optometry & Vision Science*. vol. 66, No. 9, pp. 579-590.
Atchison. Optical design of Intraocular lenses. III. On-axis performance. *Optometry & Vision Science*. vol. 66, No. 10, pp. 671-681.
Atchison. Refractive errors induced by displacement of intraocular lenses within the pseudophakic eye. *Optometry & Vision Science*. vol. 66, No. 3, pp. 146-152.
Atchison. Third-order aberrations of pseudophakic eyes. *Ophthal. Physiol. Opt.* Apr. 1989. vol. 9, pp. 205-211.
Bonnet, et al. New method of topographical ophthalmometry-its theoretical and clinical applications. *American Journal of Optometry and Archives of American Academy of Optometry*. May 1962, vol. 39, No. 5, pp. 227-251.
Guillon et al. Corneal topography: a clinical model, *Ophthal, Physiol. Opt.* 1986. vol. 6, No. 1, pp. 47-56.
El Hage et al. Contribution of the crystalline lens to the spherical aberration of the eye. *Journal of the Optical Society of America*. Feb. 1973, vol. 63, No. 2, pp. 205-211.
Kiely et al. The mean shape of the human cornea. *Optica ACTA*. 1982. vol. 29, No. 8, pp. 1027-1040.
Lindsay, et al. Descriptors of corneal shape. *Optometry and Vision Science*. Feb. 1998. vol. 75, No. 2, pp. 156-158.
Lotmar. Theoretical eye model with aspherics. *Journal of the Optical Society of America*. Nov. 1971. vol. 61, No. 11, pp. 1522-1529.
Mandell, O.D., Ph.D., et al. *Mathematical model of the corneal contour*, School of Optometry, University of California, Berkeley. pp.183-197.
Smith et al. The spherical aberration of intra-ocular lenses. *Ophthal. Physiol. Opt.* Jul. 1988. vol. 8, pp. 287-294.
Townsley. *New knowledge of the corneal contour*. pp. 38-43.

* cited by examiner

*Primary Examiner*—Jordan M. Schwartz
*Assistant Examiner*—Jessica Stultz
(74) *Attorney, Agent, or Firm*—AMO Groningen B.V.

(57) ABSTRACT

An intraocular correction lens has at least one aspheric surface which when its aberrations are expressed as a linear combination of polynomial terms, is capable of, in combination with a lens in the capsular bag of an eye, reducing similar such aberration terms obtained in a wavefront having passed the cornea, thereby obtaining an eye sufficiently free from aberrations.

21 Claims, No Drawings

METHODS OF OBTAINING OPHTHALMIC LENSES PROVIDING THE EYE WITH REDUCED ABERRATIONS

RELATED APPLICATION

The present application is a divisional of application Ser. No. 10/027,703 filed Dec. 21, 2001 now U.S. Pat. No. 6,705,729, which claims the benefit of Provisional Application No. 60/259,981, filed Jan. 5, 2001.

FIELD OF INVENTION

The present invention relates to methods of designing and selecting ophthalmic lenses that provide the eye with reduced aberrations as well as lenses capable of providing such visual improvements.

BACKGROUND OF THE INVENTION

Beside first order defocus and astigmatism of the eye a number of other vision defects could be present. For example aberrations of different orders occur when a wavefront passes a refracting surface. The wavefront itself becomes aspheric when it passes an optical surface that has imperfections and vision defects occur when an aspheric wavefront falls on the retina. Both the cornea and the lens in the capsular bag contribute thus to these types of vision defects if they deviate from being perfect or perfectly compensating optical elements. The term aspheric will in this text include both asphericity and asymmetry. An aspheric surface could be either a rotationally symmetric or a rotationally asymmetric surface and/or an irregular surface, i.e all surfaces not being spherical.

It is presently discussed that the visual quality of eyes having an implanted intraocular lens (IOL) is comparable with normal eyes in a population of the same age. Consequently, a 70-year-old cataract patient can only expect to obtain the visual quality of a non-cataracteous person of the same age after surgical implantation of an intraocular lens, although such lenses objectively have been regarded as optically superior to the natural crystalline lens. This result can be explained by the fact that present IOLs are not adapted to compensate for age-related defects of the optical system of the human eye. Age-related defects of the eye have also recently been investigated and it is found that contrast sensitivity significantly declines in subjects older than 50 years. These results seem to comply with the above-mentioned discussion, since the contrast sensitivity measurements indicate that individuals having undergone cataract surgery with lens implantation will not obtain a better contrast sensitivity than persons of an average age of about 60 to 70 years.

Even if intraocular lenses aimed to substitute the defective cataract lens and other ophthalmic lenses, such as conventional contact lenses or intraocular correction lenses, have been developed with excellent optical quality, it is obvious that they fail to correct for a number of aberration phenomena of the eye including age-related aberration defects.

U.S. Pat. No. 5,777,719 (Williams et al.) discloses a method and an apparatus for accurately measuring higher aberrations of the eye as an optical system with wavefront analysis. By using a Hartmann-Shack wavefront sensor, it is possible to measure higher order aberrations of the eye and using such data to find compensation for these aberrations and thereby obtain sufficient information for the design of an optical lens which can provide a highly improved optical correction. The Hartmann-Shack sensor provides means for obtaining light reflected from the retina of the eye of a subject. The wavefront in the plane of the pupil is recreated in the plane of the lenslet array of the Hartmann-Shack sensor. Each lenslet in the array is used to form an aerial image of the retinal point source on a CCD camera located at the focal plane of the array. The wave aberration of the eye, in the form of a point source produced on the retina by a laser beam, displaces each spot by an amount proportional to the local slope of the wavefront at each of the lenslets. The output from the CCD camera is sent to a computer, which then performs calculations to fit slope data to the first derivatives of 65 Zernike polynomials. From these calculations, coefficients for weighting the Zernike polynomials are obtained. The sum of the weighted Zernike polynomials represents a reconstructed wavefront distorted by the aberrations of the eye as an optical system. The individual Zernike polynomial terms will then represent different modes of aberration.

U.S. Pat. No. 5,050,981 (Roffman) discloses another method for designing a lens by calculating modulation transfer functions from tracing a large number of rays through the lens-eye system and evaluating the distribution density of the rays in the image position. This is repeatedly performed by varying at least one lens surface until a lens is found which results in a sharp focus and a minimum of image aberrations.

The methods referred to above for designing are suitable for the design of contact lenses or other correction lenses for the phakic eye which can be perfected to compensate for the aberration of the whole eye system. However, to provide improved intraocular lenses adapted to be placed between the cornea and the capsular bag, in the anterior chamber or in the posterior chamber, it would be necessary to consider the aberrations of the individual parts of the eye.

There has recently been a focus on studying the aberrations of the eye, including a number of studies of the development of these aberrations as a function of age. In one particular study, the development of the components of the eye were examined separately, leading to the conclusion that the optical aberrations of the individual components of younger eyes cancel each other out, see Optical Letters, 1998, Vol. 23(21), pp. 1713–1715. Also the article of S. Patel et al in Refractive & Corneal Surgery, 1993, Vol. 9, pages 173–181 discloses the asphericity of posterior corneal surfaces. It is suggested that the corneal data can be used together with other ocular parameters to predict the power and the asphericity of an intraocular lens with the purpose of maximizing the optical performances of the future pseudophakic eye. Furthermore, it was also recently observed by Antonio Guirao and Pablo Artal in IOVS, 1999, Vol. 40(4), S535 that the shape of the cornea changes with age and becomes more spherical. These studies indicate that cornea in the subjects provides a positive spherical aberration which increases with the age. In Vision Research, 1998, 38(2), pp. 209–229, A Glasser et al. investigated the spherical aberration of natural crystalline lenses from eyes obtained from an eye bank after that the corneas had been removed. According to the laser scanner optical method used herein it was found that the spherical aberration from an older lens (66 years) shows uncorrected (positive) spherical aberration, whereas a 10-year-old lens shows over-corrected (negative) spherical aberration.

In view of the foregoing, it is apparent that there is a need for ophthalmic lenses that are better adapted to compensate the aberrations caused by the individual surfaces of eye, such as the corneal surfaces and the surfaces of the lens in the capsular bag, and capable of better correcting aberrations other than defocus and astigmatism, as is provided with conventional ophthalmic lenses.

DESCRIPTION OF THE INVENTION

It is an object of the invention to improve the visual quality of eyes.

It is a further object of the invention to provide for methods that result in obtaining an ophthalmic lens, which provides the eye with reduced aberrations.

It is another object of the invention to provide methods of obtaining an intraocular lens capable of reducing the aberration of the eye after its implantation into the eye.

It is a further object to provide for methods of obtaining an intraocular lens capable of compensating for the aberrations resulting from optical irregularities in the corneal surfaces and the surfaces of the lens in the capsular bag.

It is a still further object of the present invention to provide an intraocular lens which, together with a lens in the capsular bag, is capable of restoring a wavefront deviating from sphericity into a substantially more spherical wavefront.

It is a further object of the invention to provide an intraocular lens, which improves the visual quality for patients who have undergone a corneal surgery or who have corneal defects or diseases.

The present invention generally relates to methods of obtaining an ophthalmic lens that is capable of reducing the aberrations of the eye. By aberrations in this context is meant wavefront aberrations. This is based on the understanding that a converging wavefront must be perfectly spherical to form a point image, i.e. if a perfect image shall be formed on the retina of the eye, the wavefront having passed the optical surfaces of the eye, such as the cornea and the natural lens must be perfectly spherical. An aberrated image will be formed if the wavefront deviates from being spherical and this is the case when it has passed a non perfect lens system. The wavefront aberration can be expressed in mathematical terms in accordance with different approximate models as is explained in textbook references, such as M. R. Freeman Optics, Tenth Edition, 1990.

In a first embodiment, the present invention is directed to a method of designing an intraocular lens capable of reducing aberrations of an eye after its implantation. The method comprises a first step of measuring the wavefront aberration of the uncorrected eye using a wavefront sensor. The shape of at least one corneal surface in the eye is also measured using a corneal topographer. The at least one corneal surface and a lens located in the capsular bag of the eye comprising said cornea are then characterized as a mathematical model and by employing this mathematical model the resulting aberrations of the corneal surface and the lens in the capsular bag are calculated. The lens in the capsular bag can be either the natural lens or an implanted lens of any kind. Hereafter the lens in the capsular bag will be called the capsular bag lens. An expression of the aberrations of the cornea and the capsular bag lens is thereby obtained, i.e. the wavefront aberrations of a wavefront having passed such a corneal surface and such a lens. Dependent on the selected mathematical model, different routes to calculate the aberrations can be taken. Preferably, the corneal surface and the capsular bag lens are characterized as mathematical models in terms of a conicoid of rotation or in terms of polynomials or a combination thereof. More preferably, the corneal surface and the capsular bag lens are characterized in terms of linear combinations of polynomials. The second step of the method is to select the power of the intraocular correction lens, which is done according to conventional methods for the specific need of optical correction of the eye. From the information of steps one and two an intraocular correction lens is modeled, such that a wavefront from an optical system comprising said correction lens and the mathematical models of the cornea and the capsular bag lens obtains reduced aberrations. The optical system considered when modeling the lens typically includes the cornea, the capsular bag lens and said correction lens, but in the specific case it can also include other optical elements including the lenses of spectacles, or an artificial correction lens, such as a contact lens or an implantable correction lens depending on the individual situation.

Modeling the lens involves selection of one or several lens parameters in a system which contributes to the determination of the lens shape of a given, pre-selected refractive power. This typically involves the selection of the anterior radius and surface shape, posterior radius and surface shape, the lens thickness, the refractive index of the lens and the lens position in the eye. In practical terms, the lens modeling can be performed with data based on a correction lens described in the Swedish patent application with application number SE-0000611-4, which hereby is incorporated in this application by reference. In such a case it is preferred to deviate as little as possible from an already clinically approved model. For this reason, it may be preferred to maintain pre-determined values of the central radii of the lens, its thickness and refractive index, while selecting a different shape of the anterior or posterior surface, thus providing these surfaces to have an aspheric or asymmetric shape. According to an alternative of the inventive method, the spherical anterior surface of the conventional starting lens is modeled by selecting a suitable aspheric component. Designing aspheric surfaces of lenses is a well-known technique and can be performed according to different principles. The construction of such surfaces is explained in more detail in our parallel Swedish Patent Application 0000611-4 which is given as reference. As said before the term aspheric in this text is not restricted to symmetric surfaces. For example radially asymmetric lenses can be used to correct for coma.

The inventive method can be further developed by comparing aberrations of an optical system comprised of the mathematical models of the cornea and the capsular bag lens and the correction lens with the aberrations of the cornea and the capsular bag lens and evaluating if a sufficient reduction in aberrations is obtained. Suitable variable parameters are found among the above-mentioned physical parameters of the lens, which can be altered so to find a lens model, which deviates sufficiently from being a spherical lens to compensate for the aberrations.

The characterization of at least one corneal surface and the capsular bag lens as mathematical models and thereby establishing mathematical models of the cornea and the capsular bag lens expressing the aberrations is preferably performed by using a wavefront sensor for measuring the total aberration of the eye and direct corneal surface measurements according to well-known topographical measurement methods which serve to express the surface irregularities of the cornea into a quantifiable model that can be used with the inventive method. From these two measurements the aberration of the capsular bag lens could also be calculated and expressed in aberration terms, such as a linear combination of polynomials which represent the aberration of the capsular bag lens. The aberration of the capsular bag lens is determined either by using the wavefront aberration values of the whole eye and from these subtracting the wavefront aberration values of the cornea or alternatively by modeling the optical system in the following way—start with a model of the cornea based on corneal measurements and a "starting point" capsular bag lens, calculate the aberrations of this system, then modify the shape of the capsular bag lens until the calculated aberrations are sufficiently similar to the measured aberrations of the uncorrected eye. Corneal measurements for this purpose can be performed by the ORBSCAN® videokeratograph, as available from Orbtek, L.L.C, or by corneal topography methods, such as but not limited to EyeSys® or Humphrey Atlas®. Preferably at least the front corneal surface is measured and more preferably both front and rear corneal surfaces are measured, characterized and expressed in aberration terms, such as a linear combination of polynomials which represent the total corneal aberrations. According to one important aspect of the present invention, characterization of corneas and capsular bag lenses is conducted on a selected population with the purpose of expressing an average of aberrations and designing a lens from such averaged aberrations. Average aberration terms of the population can then be calculated, for example as an average linear combination of polynomials and used in the lens design method. This aspect includes selecting different relevant populations, for example in age groups, to generate suitable average corneal surfaces and capsular bag lenses to be used to comply with individual design methods. The patient will thereby obtain a lens that gives the eye substantially less aberrations when compared to a conventional lens having substantially spherical surfaces.

Preferably, the mentioned measurements also include the measurement of the refractive power of the eye. The powers of the cornea and the capsular bag lens as well as the axial eye length are typically considered for the selection of the lens power in the inventive design method.

Also preferably, the wavefront aberrations herein are expressed as a linear combination of polynomials and the optical system comprising the mathematical model of the cornea and the capsular bag lens and the modeled intraocular correction lens provides for a wavefront having obtained a substantial reduction in aberrations, as expressed by one or more such polynomial terms. In the art of optics, several types of polynomial terms are available to skilled persons for describing aberrations. Suitably, the polynomials are Seidel or Zernike polynomials. According to the present invention Zernike polynomials preferably are employed.

The technique of employing Zernike terms to describe wavefront aberrations originating from optical surfaces deviating from being aberration free is a state of the art technique and can be employed for example with a Hartmann-Shack sensor as outlined in J. Opt. Soc. Am., 1994, Vol. 11(7), pp. 1949–57. It is also well established among optical practitioners that the different Zernike terms signify different aberration phenomena including defocus, astigmatism, coma and spherical aberration as well as higher order forms of these aberrations. In an embodiment of the present method, the corneal surface and capsular bag lens measurements results in that a corneal surface shape and a capsular bag lens shape can be expressed as linear combinations of Zernike polynomials (as described in Equation (1)), wherein $Z_i$ is the i-th Zernike term and $a_i$ is the weighting coefficient for this term. Zernike polynomials are a set of complete orthogonal polynomials defined on a unit circle. Below, Table 1 shows the first 15 Zernike terms up to the fourth order and the aberrations each term signifies.

$$z(\rho, \theta) = \sum_{i=1}^{15} a_i Z_i \quad (1)$$

In equation (1), $\rho$ and $\theta$ represent the normalized radius and the azimuthal angle, respectively.

TABLE 1

| $a_i$ | $Z_i (\rho, \theta)$ | |
|---|---|---|
| $a_1$ | 1 | piston |
| $a_2$ | $2\rho\cos\theta$ | Tilt x |
| $a_3$ | $2\rho\sin\theta$ | Tilt y |
| $a_4$ | $\sqrt{3}(2\rho^2 - 1)$ | defocus |
| $a_5$ | $\sqrt{6}(\rho^2 \sin 2\theta)$ | Astigmatism $1^{st}$ order (45°) |
| $a_6$ | $\sqrt{6}(\rho^2 \cos 2\theta)$ | Astigmatism $1^{st}$ order (0°) |
| $a_7$ | $\sqrt{8}(3\rho^3 - 2\rho) \sin\theta$ | Coma y |
| $a_8$ | $\sqrt{8}(3\rho^3 - 2\rho) \cos\theta$ | Coma x |
| $a_9$ | $\sqrt{8}(\rho^3 \sin 3\theta)$ | Trifoil 30° |
| $a_{10}$ | $\sqrt{8}(\rho^3 \cos 3\theta)$ | Trifoil 0° |
| $a_{11}$ | $\sqrt{5}(6\rho^4 - 6\rho^2 + 1)$ | spherical aberration |
| $a_{12}$ | $\sqrt{10}(4\rho^4 - 3\rho^2) \cos 2\theta$ | Astigmatism $2^{nd}$ order (0°) |
| $a_{13}$ | $\sqrt{10}(4\rho^4 - 3\rho^2) \sin 2\theta$ | Astigmatism $2^{nd}$ order (45°) |
| $a_{14}$ | $\sqrt{10}(\rho^4 \cos 4\theta)$ | Tetrafoil 0° |
| $a_{15}$ | $\sqrt{10}(\rho^4 \sin 4\theta)$ | Tetrafoil 22.5° |

Conventional optical correction with intraocular lenses will only comply with the fourth tern of an optical system comprising the eye with an implanted lens. Glasses, contact lenses and intraocular lenses provided with correction for astigmatism can further comply with terms five and six and thus substantially reduce Zernike polynomials referring to astigmatism.

The inventive method further includes to calculate the aberrations resulting from an optical system comprising said modeled intraocular correction lens and said mathematical models of the cornea and the capsular bag lens and expressing it in a linear combination of polynomials and to determine if the intraocular correction lens has provided sufficient reduction in aberrations. If the reduction in aberrations is found to be insufficient, the lens will be re-modeled until one or several of the polynomial terms are sufficiently reduced. Remodeling the lens means that at least one of the conventional lens design parameters is changed. These include the anterior surface shape and/or central radius, the posterior surface shape and/or central radius, the thickness of the lens and its refractive index. Typically, such remodeling includes changing the curvature of a lens surface so it deviates from being a perfect sphere. There are several tools available in lens design that are useful to employ with the design method, such as OSLO version 5 see Program Reference, Chapter 4, Sinclair Optics 1996.

According to a preferred aspect of the first embodiment, the inventive method comprises expressing the shape of at least one corneal surface and a capsular bag lens as linear combinations of Zernike polynomials and thereby determining the corneal and capsular bag lens wavefront Zernike coefficients, i.e. the coefficient to each of the individual Zernike polynomials that is selected for consideration. The correction lens is then modeled so that an optical system comprising said modeled correction lens and the mathematical models of the cornea and the capsular bag lens provides a wavefront having a sufficient reduction of selected Zernike coefficients. The method can optionally be refined with the further steps of calculating the Zernike coefficients of the Zernike polynomials representing a wavefront resulting from an optical system comprising the modeled intraocular correction lens and the mathematical models of the cornea and the capsular bag lens and determining if the lens has provided a sufficient reduction of the cornea and the capsular bag lens wavefront Zernike coefficients; and optionally re-modeling said lens until a sufficient reduction in said coefficients is obtained. Preferably, in this aspect the method considers Zernike polynomials lip to the 4th order and aims to sufficiently reduce Zernike coefficients referring to spherical aberration and/or astigmatism terms. It is particularly preferable to sufficiently reduce the 11th Zernike coefficient of a wavefront from an optical system comprising the mathematical models of the cornea and the capsular bag lens and said modeled intraocular correction lens, so as to obtain an eye sufficiently free from spherical aberration. Alternatively, the design method can also include reducing higher order aberrations and thereby aiming to reduce Zernike coefficients of higher order aberration terms than the $4^{th}$ order.

When designing lenses based on corneal and capsular bag lens characterizations from a selected population, preferably the corneal surfaces and the capsular bag lens of each individual are expressed in Zernike polynomials and the Zernike coefficients are determined. From these results average Zernike coefficients are calculated and employed in the design method, aiming at a sufficient reduction of selected such coefficients. It is to be understood that the resulting lenses arriving from a design method based on average values from a large population have the purpose of substantially improving visual quality for all users. A lens having a total elimination of an aberration term based on an average value may consequently be less desirable and leave certain individuals with an inferior vision than with a conventional lens. For this reason, it can be suitable to reduce the selected Zernike coefficients only to a certain degree or to a predetermined fraction of the average value.

According to another approach of the inventive design method, corneal and capsular bag lens characterizations of a selected population and the resulting linear combinations of polynomials, e.g. Zernike polynomials, expressing each individual corneal and capsular bag lens aberrations can be compared in terms of coefficient values. From this result, a suitable value of the coefficients is selected and employed in the inventive design method for a suitable lens. In a selected population having aberrations of the same sign such a coefficient value can typically be the lowest value within the selected population and the lens designed from this value would thereby provide improved visual quality for all individuals in the group compared to a conventional lens.

According to another embodiment, the present invention is directed to the selection of an intraocular lens of refractive power, suitable for the desired optical correction that the patient needs, from a plurality of lenses having the same power but different aberrations. The selection method is similarly conducted to what has been described with the design method and involves the characterization of at least one corneal surface and one capsular bag lens with mathematical models by means of which the aberrations of the corneal surface and the capsular bag lens is calculated. The optical system of the selected correction lens and the mathematical models of the corneal and the capsular bag lens is then evaluated so as to consider if sufficient reduction in aberrations is accomplished by calculating the aberrations of a wavefront arriving from such a system. If an insufficient correction is found a new lens is selected, having the same power, but different aberrations. The mathematical models employed herein are similar to those described above and the same characterization methods of the corneal surfaces and the capsular bag lens can be employed.

Preferably, the aberrations determined in the selection are expressed as linear combinations of Zernike polynomials and the Zernike coefficients of the resulting optical system comprising the mathematical models of the cornea and the capsular bag lens and the selected correction lens are calculated. From the coefficient values of the system, it can be determined if the intraocular correction lens has sufficiently balanced the corneal and capsular bag lens aberration terms, as described by the Zernike coefficients of the optical system. If no sufficient reduction of the desired individual coefficients are found these steps can be iteratively repeated by selecting a new correction lens of the same power but with different aberrations, until a lens capable of sufficiently reducing the aberrations of the optical system is found. Preferably at least 15 Zernike polynomials up to the $4^{th}$ order are determined. If it is regarded as sufficient to correct for spherical aberration, only the spherical aberration terms of the Zernike polynomials for the optical system of cornea and capsular bag lens and intraocular correction lens are corrected. It is to be understood that the intraocular correction lens shall be selected so a selection of these terms becomes sufficiently small for the optical system comprising correction lens and cornea and capsular bag lens. In accordance with the present invention, the $11^{th}$ Zernike coefficient, $a_{11}$, can be substantially eliminated or sufficiently close to zero. This is a prerequisite to obtain an intraocular correction lens that sufficiently reduces the spherical aberration of the eye. The inventive method can be employed to correct for other types of aberrations than spherical aberration by considering other Zernike coefficients in an identical manner, for example those signifying astigmatism, coma and higher order aberrations. Also higher order aberrations can be corrected dependent on the number of Zernike polynomials elected to be a part of the modeling, in which case a correction lens can be selected capable of correcting for higher order aberrations than the $4^{th}$ order.

According to one important aspect, the selection method involves selecting correction lenses from a kit of correction lenses having lenses with a range of power and a plurality of lenses within each power having different aberrations. In one example the correction lenses within each power have anterior surfaces with different aspheric components. If a first correction lens does not exhibit sufficient reduction in aberration, as expressed in suitable Zernike coefficients, then a new correction lens of the same power, but with a different surface is selected. The selection method can if necessary be iteratively repeated until the best correction lens is found or the studied aberration terms are reduced below a significant borderline value. In practical means, the Zernike terms obtained from the corneal and capsular bag lens examination will be directly obtained by the ophthalmic surgeon and by means of an algorithm will be compared to known Zernike terms of the correction lenses in the kit. From this comparison the most suitable correction lens in the kit can be found and implanted.

The present invention further pertains to an intraocular correction lens having at least one aspheric surface capable of transferring a wavefront having passed through the cornea of the eye into a wavefront that when it after passing the correction lens passes the capsular bag lens is transferred into a substantially spherical wavefront with its center at the retina of the eye. Preferably, the wavefront is substantially spherical with respect to aberration terms expressed in rotationally symmetric Zernike terms up to the fourth order.

In accordance with an especially preferred embodiment, the invention relates to an intraocular correction lens, which when the aberration is calculated and expressed as a linear combination of Zernike polynomial terms, has an $11^{th}$ term of the fourth order with a Zernike coefficient $a_{11}$ of a value that after implantation of the correction lens sufficiently reduces the spherical aberration of a wavefront passing the eye. In one aspect of this embodiment, Zernike coefficient $a_{11}$ of the correction lens is determined so as to compensate for an average value resulting from a sufficient number of estimations of the Zernike coefficient $a_{11}$ in corneas and capsular bag lenses. In another aspect, the Zernike coefficient $a_{11}$ is determined to compensate for the individual corneal and capsular bag lens coefficient of one patient. The lens can accordingly be tailored for an individual with high precision.

The lenses according to the present invention can be manufactured with conventional methods. In one embodiment they are made from soft, resilient material, such as silicone or hydrogels. Examples of such materials are found in WO 98/17205. Manufacturing of aspheric silicone lenses or similarly foldable lenses can be performed according to U.S. Pat. No. 6,007,747. Alternatively, the lenses according to the present invention can be made of a more rigid material, such as poly(methyl)methacrylate. As described in SE-0000611-4 incorporated herein by reference, the lenses according to the present invention can be made from conventional biocompatible optically clear materials of a suitable refractive index by suitable molding technologies. Depending on the material, the lenses can be molded in one singular piece (silicones or poly(methyl)methacrylate (PMMA)) or be machined by precision milling and lathe cutting (PMMA or hydrogels). The lenses can be made from stiff materials like PMMA and similar acrylates. Alternatively, the lenses can be made of a material that is foldable or compressible like polysiloxanes, hydrogels such as polyHEMA, soft acrylates and the similar. A particularly suitable polysiloxane material is described in U.S. Pat. No. 5,306,297 and a particularly suitable hydrogel is described in U.S. Pat. No. 5,717,049. The skilled person can readily identify alternative materials and manufacturing methods, which will be suitable to employ to produce the inventive aberration reducing lenses.

In one preferred embodiment of the invention the intraocular correction lens is adapted to be implanted in the posterior chamber of the eye between the iris and the capsular bag. The correction lens according to this embodiment comprises preferably a centrally located optical part capable of providing an optical correction and a peripherally located supporting element capable of maintaining said optical part in said central location, said optical part and said support element together having a concave posterior surface which is part of a non-spherical surface, the intersection between said non-spherical surface and any plane containing the optical axis representing a flawless curve free from discontinuities and points of inflection. Such an intraocular correction lens without the inventive aberration reduction is described in SE-0000611-4. This lens design is preferred since it is adapted to the anatomy of the eye and avoids stress to the crystalline lens. Due to its design, contacts between the natural lens and the iris are avoided or minimized.

The method of designing this preferred correction lens comprises suitably the steps of:

estimating the anterior radius of the lens in the capsular bag in its non-accommodated state;

selecting a posterior central radius of the correction lens different to that of the lens in the capsular bag in its non-accommodated state;

determining the total correction lens vault based on the data arriving from steps (i) and (ii);

selecting a flawless curve free from points of inflection representing the intersection of the posterior surface and a plane containing the optical axis so as to provide an aspheric posterior correction lens surface.

In another embodiment of the invention the correction lens is adapted to be placed in the anterior chamber of the eye and fixated to iris. The advantage of this embodiment is that the correction lens is attached to iris and will not move around and has no ability to rotate thus making it more suitable for correcting non-symmetric aberrations The present invention also relates to a method of improving the vision of an eye. According to the invention an intraocular correction lens as described above is implanted in the eye. The vision can also be further improved by providing spectacles or correction lenses outside the eye or by modulating the cornea by for example laser.

The ophthalmic lenses according to the invention can suitably be designed and produced especially for correcting for aberrations introduced by corneal surgery such as LASIC (=laser in situ keratomilensis) and PRK (=photorefractive keratectomy). The cornea and the whole eye are measured as described above on patients who have undergone corneal surgery and the correction lenses are designed from these measurements. The lenses according to the invention could also suitably be designed for patients having corneal defects or corneal diseases.

The described lenses according to the invention could either be designed for each individual or they could be designed for a group of people.

The invention also refers to a method of improving the visual quality of an eye, wherein a corneal surgery first is conducted on the eye. The cornea is then allowed to recover before a wavefront analysis of the eye is performed. If the aberrations of the eye have to be reduced a correction lens adapted for this individual is designed according to the description above. This correction lens is then implanted in the eye. Different types of corneal surgery are possible. Two common methods are LASIK and PRK, as described in Survey of Ophthalmology, 1998, Vol. 43 (2), p147–156 by J J Rowsey et al. The presently invented method will find particular advantage the perfect visual quality for individuals who have undergone corneal surgery, but have outstanding visual impairments, which are considered as difficult to reach with conventional surgery.

The invention claimed is:

1. An intraocular correction lens having at least one aspheric surface designed such that its aberrations are expressed as a linear combination of polynomial terms, and in combination with a lens in the capsular bag of an eye reduces similar such aberration terms obtained in a wavefront having passed the cornea, thereby obtaining an eye sufficiently free from aberrations.

2. An intraocular correction lens according to claim 1, wherein said aspheric surface is the anterior surface of the lens.

3. An intraocular correction lens according to claim 1, wherein said aspheric surface is the posterior surface of the lens.

4. An intraocular correction lens according to claim 3, wherein said polynomial terms are Zernike polynomials.

5. An intraocular correction lens according to claim 4 capable of reducing polynomial terms representing spherical aberrations and astigmatism.

6. A lens according to claim 5, capable of reducing the 11th Zernike polynomial term of the 4th order.

7. An intraocular correction lens according to claim 6 made from a soft biocompatible material.

8. An intraocular correction lens according to claim 7 made of silicone.

9. An intraocular correction lens according to claim 7 made of hydrogel.

10. An intraocular correction lens according to claim 6 made of a rigid biocompatible material.

11. An intraocular correction lens according to claim 1 adapted to be implanted in the posterior chamber bag comprising a centrally located optical part capable of providing an optical correction and a peripherally located supporting element capable of maintaining said optical part in said central location, said optical part and said support element together having a concave posterior surface which is part of a non-spherical surface, the intersection between said non-spherical surface and any plane containing the optical axis representing a flawless curve free from discontinuities and points of inflection.

12. An intraocular correction lens according to claim 11 adapted to be implanted in the anterior chamber of the eye and fixated to iris.

13. A method for improving the visual quality of an eye, comprising implanting an intraocular correction lens according to claim 1.

14. A method according to claim 13, wherein spectacles or correction lenses are provided outside the eye to further improve the visual quality.

15. A method according to claim 13, wherein the cornea of the patient receiving the intraocular correction lens has been modified by means of a laser.

16. A method according to claim 13, wherein the intraocular correction lens is implanted in the anterior chamber of the eye and fixated to iris.

17. An intraocular correction lens according to claim 11 made from a soft biocompatible material.

18. An intraocular correction lens according to claim 17 made of silicone or hydrogel.

19. An intraocular correction lens according to claim 11 made of a rigid biocompatible material.

20. An intraocular correction lens according to claim 11 made of acrylate material.

21. An intraocular correction lens according to claim 1 made of acrylate material.

* * * * *